US012573470B2

(12) United States Patent
Bose et al.

(10) Patent No.: US 12,573,470 B2
(45) Date of Patent: Mar. 10, 2026

(54) IDENTIFYING THERAPEUTIC BIOMARKERS ASSOCIATED WITH COMPLEX DISEASES

(71) Applicant: INTERNATIONAL BUSINESS MACHINES CORPORATION, Armonk, NY (US)

(72) Inventors: Aritra Bose, White Plains, NY (US); Daniel Enoch Platt, Putnam Valley, NY (US); Niina Haiminen, Valhalla, NY (US); Laxmi Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 905 days.

(21) Appl. No.: 17/453,221

(22) Filed: Nov. 2, 2021

(65) Prior Publication Data

US 2023/0132849 A1 May 4, 2023

(51) Int. Cl.
| | |
|---|---|
| *G16B 20/00* | (2019.01) |
| *G06N 5/02* | (2023.01) |
| *G16B 25/10* | (2019.01) |
| *G16B 40/00* | (2019.01) |

(52) U.S. Cl.
CPC .............. *G16B 20/00* (2019.02); *G06N 5/02* (2013.01); *G16B 25/10* (2019.02); *G16B 40/00* (2019.02)

(58) Field of Classification Search
CPC ........ G16B 20/00; G16B 25/10; G16B 40/00; G06N 5/02
See application file for complete search history.

(56) References Cited

U.S. PATENT DOCUMENTS

| | | | |
|---|---|---|---|
| 2005/0015827 A1* | 1/2005 | Podlich | C12Q 1/68 |
| | | | 800/278 |
| 2011/0246409 A1* | 10/2011 | Mitra | G06F 17/18 |
| | | | 702/179 |
| 2017/0373946 A1* | 12/2017 | Lewandowski | H04L 67/10 |
| 2019/0096526 A1 | 3/2019 | Hirsch | |

(Continued)

FOREIGN PATENT DOCUMENTS

| | | |
|---|---|---|
| CN | 104270283 B | 11/2017 |
| WO | 2015173435 A1 | 11/2015 |
| WO | WO-2019172747 A1 * | 9/2019 ............. A61Q 19/08 |

OTHER PUBLICATIONS

Ding et al. "Detection of Lung Cancer with Breath Biomarkers Based on SVM Regression," 2009 Fifth International Conference on Natural Computation, 2009. pp. 131-138. (Year: 2009).*

(Continued)

*Primary Examiner* — Kyle R Stork
(74) *Attorney, Agent, or Firm* — Elliot J. Shine

(57) ABSTRACT

A method, computer system, and a computer program product for biomarker identification is provided. The present invention may include generating a plurality of higher-order joint cumulants based on an input data matrix. The present invention may include identifying one or more significant higher-order joint cumulant groups from the plurality of higher-order joint cumulants. The present invention may include embedding the one or more significant higher-order joint cumulant groups into a lower dimensional network. The present invention may include identifying one or more biomarkers.

20 Claims, 5 Drawing Sheets

(56)                References Cited

U.S. PATENT DOCUMENTS

2019/0102514 A1*    4/2019    Parida ..................... G16B 40/20
2021/0319884 A1*    10/2021   Day ........................ G16H 40/20

OTHER PUBLICATIONS

Gunderson et al. "Introducing Graph Cumulants: What is the Variance of Your Social Network?," Apr. 14, 2020, pp. 1-69. (Year: 2020).*

Harris, Frank E. "Cumulant-Based Approximations to Reduce Density Matrices," International Journal of Quantum Chemistry, vol. 90, 2002, pp. 105-113. (Year: 2002).*

Chang et al. "A meta-analysis of genome-wide association studies identifies 17 new Parkinson's disease risk loci," Nature Genetics, vol. 49, No. 10, Oct. 2017, pp. 1511-1518. (Year: 2017).*

Roden et al., "Integrating electronic health record genotype and phenotype datasets to transform patient care," Dec. 14, 2015, Clinical Pharmacology & Therapeutics, vol. 99, Issue 3 Big Data, pp. 298-305. (Year: 2015).*

Fisher, R.A. et al. "Statistical Tables For Biological, Agricultural, and Medical Research," Oliver and Boyd, 1963, pp. 1-146. (Year: 1963).*

Bose, et al., "CuNA: Cumulant-based Network Analysis of genotype-phenotype relationships in Parkinson's," GitHub, Mar. 9, 2021, 4 pages, Retrieved from the Internet: <URL: https://github.com/ComputationalGenomics/CuNA>.

Brunel, et al., "The Central Role of KNG1 Gene as a Genetic Determinant of Coagulation Pathway-Related Traits: Exploring Metaphenotypes," Plos One [research article], Dec. 22, 2016, 14 pages, DOI:10.1371/journal.pone.0167187, Retrieved from the Internet: <URL: https://journals.plos.org/plosone/article?id=10.1371/journal.pone.0167187>.

Bürger, "Moments, cumulants, and polygenic dynamics," Journal of Mathematical Biology, 1991, pp. 199-213, vol. 30, Issue 2, Retrieved from the Internet: <URL: https://link.springer.com/article/10.1007/BF00160336>.

Dey, et al., "A Fast and Accurate Algorithm to Test for Binary Phenotypes and Its Application to PheWAS," American Journal of Human Genetics AJHG [online], Jun. 8, 2017, pp. 37-49, vol. 1, Issue 1, DOI:https://doi.org/10.1016/j.ajhg.2017.05.014, Retrieved from the Internet: <URL: https://www.cell.com/ajhg/fulltext/S0002-9297(17)30201-X>.

Durstenfeld, "Algorithm 235: Random permutation," Communications of the ACM [article], Jul. 1967, vol. 7, Issue 7, Retrieved form the Internet: <URL: https://doi.org/10.1145/364520.364540>.

Ertekin-Taner, "Gene expression endophenotypes: a novel approach for gene discovery in Alzheimer's disease." Molecular Neurodegeneration, 2011, 18 pages, vol. 6, Issue 31, Retrieved from the Internet: <URL: https://molecularneurodegeneration.biomedcentral.com/articles/10.1186/1750-1326-6-31>.

Grace Period Disclosure: "CuNA: Cumulant-based Network Analysis of genotype-phenotype associations in Parkinson's Disease", [Aritra Bose, Daniel E. Platt, Niina Haiminen, and Laxmi Parida], Published Aug. 5, 2021, 31 pages.

Hall, et al., "A new role for endophenotypes in the GWAS era: functional characterization of risk variants," Harvard review of psychiatry [manuscript], 11 pages, vol. 18, Issue 1, DOI: 10.3109/10673220903523532, Retrieved from the Internet: <URL: https://www.ncbi.nlm.nih.gov/pmc/articles/PMC3586547/>.

Leopold, et al., "Emerging Role of Precision Medicine in Cardiovascular Disease," Circulation Research [research paper], Apr. 2018, pp. 1302-1315, DOI: 10.1161/CIRCRESAHA.117.310782, Retrieved from the Internet: <URL: https://www.ahajournals.org/doi/full/10.1161/CIRCRESAHA.117.310782>.

Lin, et al., "MetaPhat: Detecting and Decomposing Multivariate Associations From Univariate Genome-Wide Association Statistics," Frontiers in Genetics [journal], May 15, 2020, 10 pages, vol. 11, Article 431, ISSN: 1664-8021, DOI: 10.3389/fgene.2020.00431, Retrieved from the Internet: <URL: https://www.frontiersin.org/articles/10.3389/fgene.2020.00431/full>.

Mell, et al., "The NIST Definition of Cloud Computing", National Institute of Standards and Technology, Special Publication 800-145, Sep. 2011, 7 pages.

Parida, et al., "Redescription Mining: Structure Theory and Algorithms," AAAI.org [paper], 2005, pp. 837-844, vol. 05, Retrieved from the Internet: <URL: https://www.aaai.org/Papers/AAAI/2005/AAAI05-132.pdf>.

Percus, Correlation inequalities for Ising spin lattices. Communications in Mathematical Physics, 1975, pp. 283-308, vol. 40, Retrieved from the Internet: <URL: https://doi.org/10.1007/BF01610004>.

Platt, et al., "Characterizing redescriptions using persistent homology to isolate genetic pathways contributing to pathogenesis." BMC Systems Biology, 2016, vol. 10, Issue S10, pp. 107-119, Retrieved from the Internet: <URL: https://bmcsystbiol.biomedcentral.com/articles/10.1186/s12918-015-0251-2>.

Zhang, et al., "Inclusion of endophenotypes in a standard GWAS facilitate a detailed mechanistic understanding of genetic elements that control blood lipid levels," Scientific Reports [article], 2020, 14 pages, vol. 10, Retrieved from the Internet: <URL: https://doi.org/10.1038/s41598-020-75612-6>.

Zhou, "Computational and Statistical Approaches for Large-Scale Genome-Wide Association Studies." University of Michigan [dissertation], 2018, 206 pages, Retrieved from the Internet: <URL: https://deepblue.lib.umich.edu/handle/2027.42/144097>.

Zwir, at al., Analysis of differentially-regulated genes within a regulatory network by GPS genome navigation, Bioinformatics [original paper], 2005, pp. 4073-4083, vol. 21, No. 22, DOI: 10.1093/bioinformatics/bti672, Retrieved from the Internet: <URL: https://academic.oup.com/bioinformatics/article/21/22/4073/194554?login=true>.

* cited by examiner

200

IDENTIFYING THERAPEUTIC BIOMARKERS ASSOCIATED WITH COMPLEX DISEASES

STATEMENT REGARDING PRIOR DISCLOSURES BY THE INVENTOR OR A JOINT INVENTOR

The following disclosure are submitted under 35 U.S.C. 102(b)(1)(A): DISCLOSURE: [CuNA: Cumulant-based Network Analysis of genotype-phenotype associations in Parkinson's Disease, Aritra Bose, Daniel E. Platt, Niina Haiminen, and Laxmi Parida, Aug. 5, 2021, p. 1-31.]

BACKGROUND

The present invention relates generally to the field of computing, and more particularly to biomarker identification.

In medicinal biology, a biomarker may be a measurable indicator of the severity and/or presence of a particular disease state and/or some other physiological state of an organism. The measurable indicator may be chemical, physical, and/or biological in nature, and the measurement may be functional, physiological, biochemical, cellular, and/or molecular. In medicinal biology, biomarkers may be utilized along with at least demographic, phenotypic, behavioral, and environmental exposures in evaluating and/or determining the most effective therapeutic regimen for a patient by at least, measuring disease progression, enabling early diagnosis, identifying drug targets, establishing long-term susceptibility risks, amongst other information that may be used by physicians and/or researchers in determining the most effective therapeutic regimen.

Understanding how biomarkers and environmental factors influence complex disease symptoms may be critical in determining the relationship between the phenotype and genotype for complex diseases, however, understanding how biomarkers influence complex disease symptoms may be complicated by the interplay between genetic, environmental, and/or demographic influences, amongst other factors.

SUMMARY

Embodiments of the present invention disclose a method, computer system, and a computer program product for biomarker identification. The present invention may include generating a plurality of higher-order joint cumulants based on an input data matrix. The present invention may include identifying one or more significant higher-order joint cumulant groups from the plurality of higher-order joint cumulants. The present invention may include embedding the one or more significant higher-order joint cumulant groups into a lower dimensional network. The present invention may include identifying one or more biomarkers.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
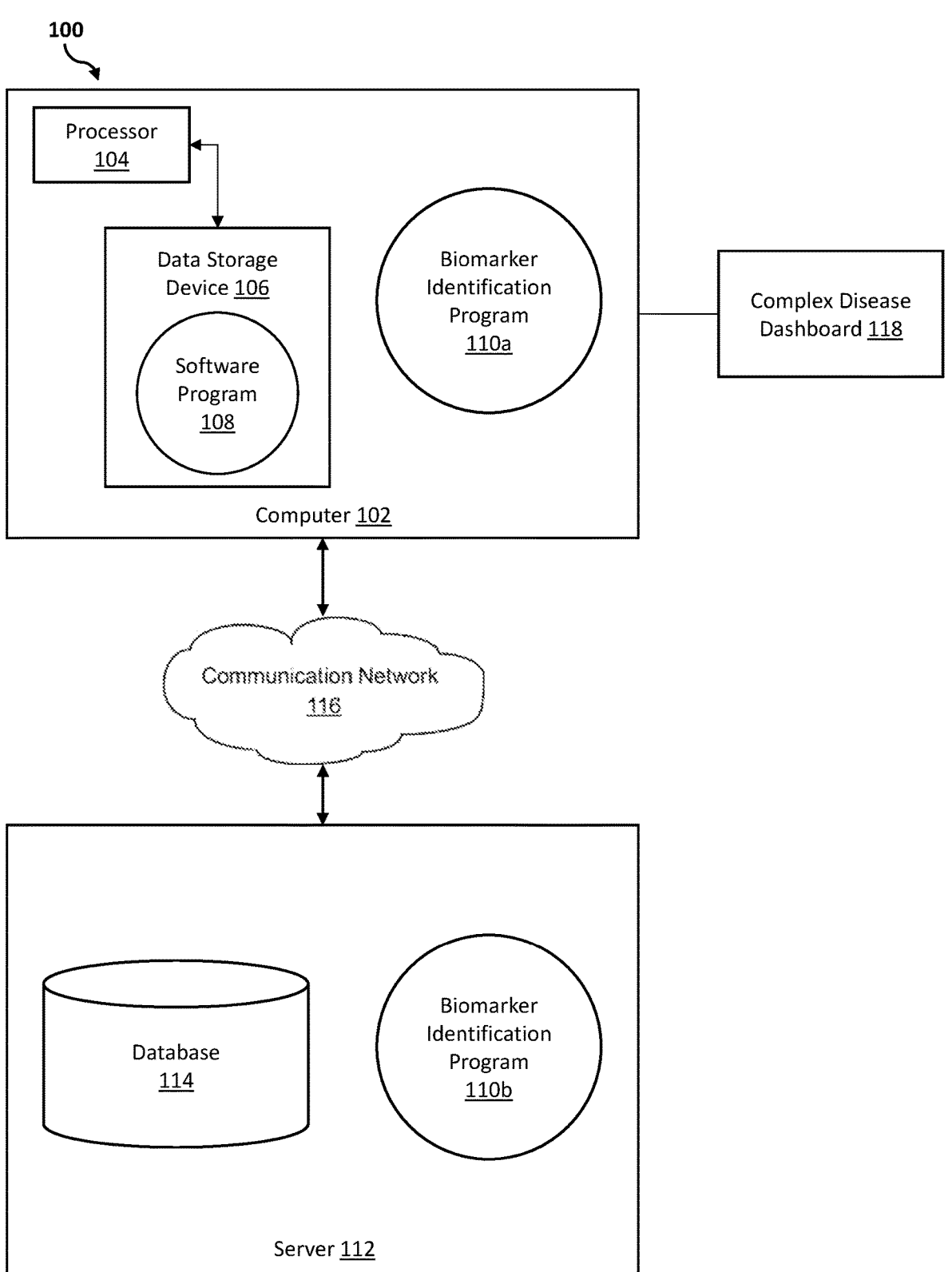
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The data may be secured, with the external storage participating in two-factor authentication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages, and interpreted languages implemented on virtual machines, such as Python and Java. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for biomarker identification. As such, the present embodiment has the capacity to improve the technical field of complex disease genetics by identifying biomarkers associated with complex diseases for utilization in targeted drug delivery and/or personalized medicine treatments. More specifically, the present invention may include generating a plurality of higher-order joint cumulants based on an input data matrix. The present invention may include identifying one or more significant higher-order joint cumulant groups from the plurality of higher-order joint cumulants. The present invention may include embedding the one or more significant higher-order joint cumulant groups into a lower dimensional network. The present invention may include identifying one or more biomarkers.

As described previously, In medicinal biology, a biomarker may be a measurable indicator of the severity and/or presence of a particular disease state and/or some other physiological state of an organism. The measurable indicator may be chemical, physical, and/or biological in nature, and the measurement may be functional, physiological, biochemical, cellular, and/or molecular. In medicinal biology, biomarkers may be utilized along with at least demographic, phenotypic, behavioral, and environmental exposures in evaluating and/or determining the most effective therapeutic regimen for a patient by at least, measuring disease progression, enabling early diagnosis, identifying drug targets, establishing long-term susceptibility risks, amongst other information that may be used by physicians and/or researchers in determining the most effective therapeutic regimen.

Understanding how biomarkers and environmental factors influence complex disease symptoms may be critical in determining the relationship between the phenotype and genotype for complex diseases, however, understanding how biomarkers influence complex disease symptoms may be complicated by the interplay between genetic, environmental, and/or demographic influences, amongst other factors.

Therefore, it may be advantageous to, among other things, generate a plurality of higher-order joint cumulants based on an input data matrix, identify one or more significant higher-order cumulant groups from the plurality of higher order cumulants, embed the significant edges supported by one or more significant higher-order joint cumulant groups into a lower dimensional network, and identify one or more biomarkers.

According to at least one embodiment, the present invention may improve the ability to obtain biological insights and/or targeted genes for a group of phenotypes which may be related due to an underlying state of a disease.

According to at least one embodiment, the present invention may improve the computation of higher-order genotype-phenotype interactions by using cumulants and utilizing measures of significance with p-values and/or z-scores to reduce false positives.

According to at least one embodiment, the present invention may improve obtaining clusters of biological markers associated with a group of phenotypes by embedding higher-order significant genotype-phenotype interactions in a network and performing community-based detection.

According to at least one embodiment, the present invention may improve the ability to provide drug therapy information and/or pathway hypotheses in a complex disease dashboard based on multi-omics data.

According to at least one embodiment, the present invention may improve the detection of genes associated with complex diseases by using a Cumulant-based Network Analysis (CuNA) algorithm to generate a network from higher-order relationships between expression quantitative Trait Loci (eQTL) and phenotypes as captured by cumulants.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a biomarker identification program 110a. The networked computer environment 100 may also include a server 112 that is enabled to run a biomarker identification program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer

102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the biomarker identification program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the biomarker identification program 110a, 110b (respectively) to maintain higher order feature interactions in a lower dimensional network. The biomarker identification method is explained in more detail below with respect to FIG. 2.

Figure 2:
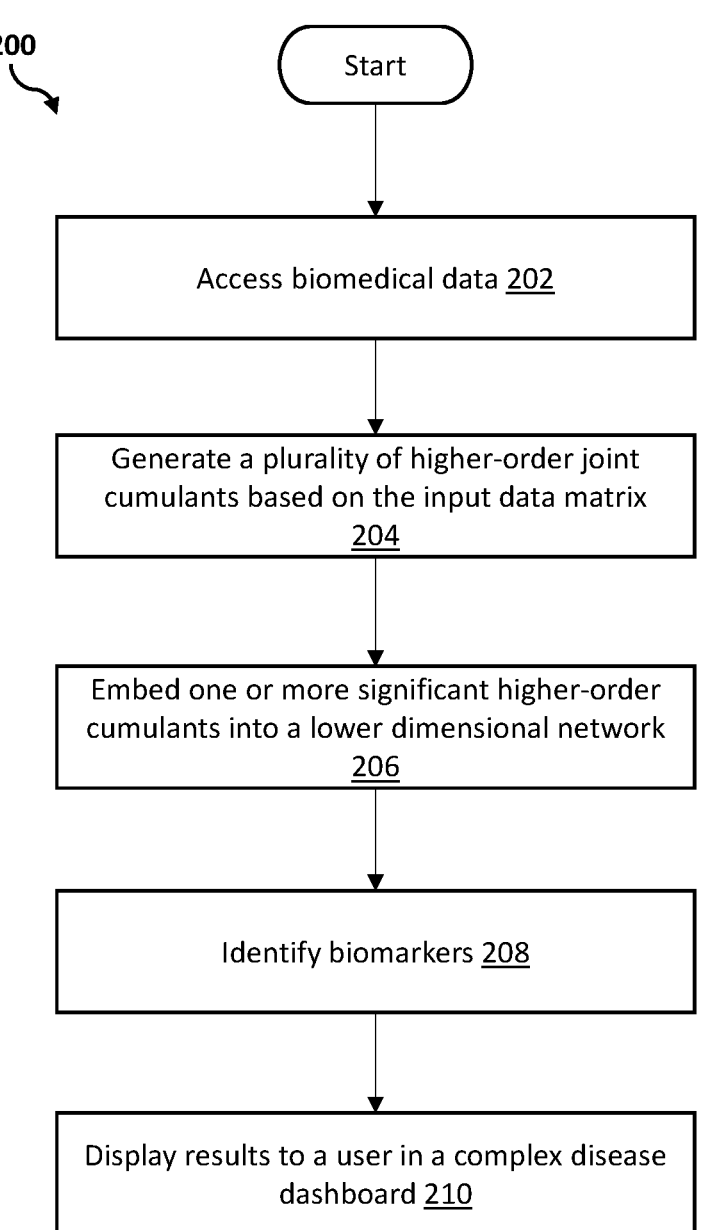
FIG. 2 is an operational flowchart illustrating a process for biomarker identification according to at least one embodiment.

Referring now to FIG. 2, an operational flowchart illustrating the exemplary biomarker identification process 200 used by the biomarker identification program 110a and 110b (hereinafter biomarker identification program 110) according to at least one embodiment is depicted.

At 202, the biomarker identification program 110 accesses biomedical data. The biomedical data may be accessed from a knowledge corpus (e.g., database 114) maintained by the biomarker identification program 110 and/or accessed from one or more publicly available resources, such as, but not limited to, one or more clinical data repositories (CDRs). The biomarker identification program 110 may access the biomedical data associated with at least a complex disease, one or more traits of interest, a patient profile, amongst other associations. The complex disease may be characterized by one or more traits of interests (e.g., phenotypes).

The biomedical data may include at least, one or more of, clinical data, omics data, and/or traits of interest. Traits of interest may be represented as outcome data. The biomedical data may only be accessed by the biomarker identification program 110 from the knowledge corpus (e.g., database 114) and/or accessed from the one or more publicly available resources with consent from a patient population and/or consent from an entity maintaining the one or more publicly available resources. Clinical data may include, but is not limited to including, electronic health records (EHRs), diet data, lifestyle/behavioral data, demographics, medications, and/or environmental exposures, amongst other patient-centric health data, for a patient population. The outcome data may be selected by a user (e.g., genetic counselor, doctor, patient, researcher, patient, medical professional) of the biomarker identification program 110 depending on at least the complex disease of interest, stages of the complex disease, symptoms, and/or traits of interest for the complex disease. The outcome data may be selected by the user (e.g., genetic counselor, doctor, patient, researcher, patient, medical professional) of the biomarker identification program 110 in a complex disease dashboard 118. The complex disease dashboard 118 may be displayed by the biomarker identification program 110 in at least an internet browser, a dedicated software application, or as an integration with a third party software application. For example, the user (e.g., genetic counselor, doctor, patient, researcher, patient, medical professional) of the biomarker identification program 110 may limit the clinical data accessed by the biomarker identification program 110 to a particular complex disease, such as, but not limited to, Parkinson's Disease, Alzheimer's Disease, Cardiovascular Disease, cancer, neurological disorders, amongst other complex diseases. The biomarker identification program 110 may not be limited to the complex diseases stated herein. In this example, the user (e.g., genetic counselor, doctor, patient, researcher, patient, medical professional) may further limit the clinical data to a particular stage of the complex disease, such as Stage 2 Parkinson's Disease, and/or non-motor symptoms.

The omics data may be a multi-omics data set, the multi-omics data set may include, but is not limited to including, genomic data sets (e.g., coding and non-coding regions of the genome), proteomic data sets, transcriptomic data sets, epigenomic data sets, metabolomic data sets, and/or microbiome data sets (i.e., meta-genome and/or meta-transcriptome, depending on how the microbiome data sets may be sequenced), amongst other omics data sets.

The biomarker identification program 110 may generate an input data matrix based on the biomedical data. The biomarker identification program 110 may generate the input data matrix by processing the biomedical data using at least one or more association methods. The one or more association methods utilized by the biomarker identification program 110 may depend on the omics data of the biomedical data. The one or more association methods may include, but are not limited to including, genome wide association studies (GWAS) analysis, whole-exome sequencing (WES), proteome-wide analysis of single nucleotide polymorphisms (SNPs), transcriptome-wide association studies (TWAS) analysis, amongst other association methods. For example, if the omics data included genomic data sets and/or transcriptomic data sets, the biomarker identification program 110 may utilize a GWAS analysis and TWAS analysis in processing the biomedical data to generate the input data matrix. The association methods may identify loci with common genetic variants contributing to risk of a complex disease. The biomarker identification program 110 may also utilize an expression Quantitative Trait Loci (eQTL) analysis in generating the input data matrix. The eQTL analysis may be utilized by the biomarker identification program 110 in identifying associations between genes (e.g., coding and non-coding regions) and the complex disease. The eQTL analysis may differ based on the multi-omics data sets accessed by the biomarker identification program 110. The eQTL analysis may also be utilized in determining hotspots, constructing causal networks, identifying stratification in clinical data, and identifying SNPs significantly associated with gene expression, amongst other uses. For example, for Parkinson's disease the biomarker identification program 110 may perform the eQTL analysis on overlapping samples between a Ribonucleic Acid (RNA) sequence and the genomic data sets. The eQTL analysis may identify associations between genome regions (e.g., coding Deoxyribonucleic acid and non-coding deoxyribonucleic acid) and a specific gene from the transcriptome, as well as how the genomic region and the specific gene are related. The biomarker identification program 110 may integrate significant associations from the eQTL analysis and association methods utilized for Parkinson's disease phenotypes. In this example, the user may have specified in the complex disease dashboard 118 non-motor symptoms such as autonomic dysfunction, sleep disturbances, cognitive dysfunction, and/ or psychiatric disorders. The biomarker identification program 110 may extract significant cis-eGenes (e.g., underlying genes associated with an eQTL, affecting it locally), wherein the eGenes may be above a predefined statistical significance threshold, and include the eGenes as features with the biomedical data related to the complex disease.

The biomarker identification program 110 may generate the input data matrix including both the clinical and/or EHR data, such as, but not limited to, blood test readings, blood protein levels, demographic information, medications, amongst other data, as well as the associations integrated from the one or more association methods and/or eQTL analysis.

At 204, the biomarker identification program 110 generates a plurality of higher-order joint cumulants. Cumulants may be higher-order moments and/or interactions between features including multi-directional interactions between features. The cumulants of a probability distribution may be a set of quantities that may provide an alternative to moments of the probability distribution. Higher-order joint cumulants may be polynomial functions of the moments of the probability distribution, and may cancel if they are only dependent on lower-order moments.

The "order" in "higher-order" may refer to the polynomial order of the joint cumulants. A joint cumulant of just one random variable may be its expected value, and that of two random variables as their covariance. If some of the random variables are independent of all the others, then any cumulant involving two or more independent random variables may be zero. If all n random variables are the same, the join cumulant may be the n-th ordinary cumulant. In statistical mechanics, an Ursell function (e.g., connected correlation function), may be a cumulant of a random variable. Additionally, for example, the biomarker identification program 110 may utilize Percus' theorem in generating the higher-order cumulant groups. According to Percus' theorem, if you have two or more groups of variates in the joint cumulant that are independent of one another (e.g., uncorrelated), the cumulant may be zero. Even though the moments are non-zero, there may be no joint interactions among all of the variables, just among subsets of those variables.

Higher-order joint cumulant groups may be a redescription cluster of features constructed from higher-order interactions between clinical features and genes for the complex disease and/or traits of interest selected by the user in the complex disease dashboard 118 at step 202. The selected higher-order joint cumulant groups may be statistically significant higher-order measures of interactions between features.

The biomarker identification program 110 may utilize a Cumulant-based Network Analysis (CuNA) in generating the higher-order cumulant groups. The CuNA may be a variation of a Topological Data Analysis (TDA) which generates the higher-order joint cumulant groups by integrating genes implicated for the complex disease as obtained through the one or more association methods and/or the eQTL analysis with the biomedical data of the input data matrix, such as associated phenotypes and/or clinical features. As will be explained in more detail below, the biomarker identification program 110 may utilize the CuNA analysis to identify subsets of features which may influence patient groups and/or individual patients with shared underlying biological pathways.

The biomarker identification program 110 may determine one or more significant higher-order joint cumulant groups from the plurality of higher-order joint cumulants generated. The one or more significant higher-order joint cumulant groups may be determined using one or more permutation tests, such as, but not limited to, Fisher permutation tests, from the significant subsets of features from the higher-order joint cumulant groups. A permutation test (e.g., re-randomization test) may be an exact test in which the distribution of the test statistic under the null hypothesis may be obtained by calculation all the possible values of the test statistic under all possible rearrangements of observed data points. The significant subset of features may be determined based on p-values and Z-scores. In null hypothesis, significance testing, the p-value may be the probability of obtaining test results at least as extreme as the results actually observed. A small p-value may indicate that an observed extreme may be unlikely under the null hypothesis. While the Z-score may denote the result in standard deviations away from an arithmetic mean under null hypotheses.

The one or more permutation tests may utilize one or more algorithms, including at least, the Fisher-Yates shuffle for randomization. The one or more permutation tests may be performed on the biomedical data in determining a relationship between features. These permutation tests may be compared to the permutation tests conducted using the input data matrix, the input data matrix including the associations integrated from the one or more association methods and/or the eQTL analysis. Accordingly, the one or more significant higher-order cumulant groups may include p-values and Z-scores above a significance threshold. The significance threshold may be p-values and Z-scores in which the probability of an association between two features exists exceeds a given variable for noise. For example, the significance threshold p-value may be $p < 1e\text{-}6$ and $Z > 3$. In this example, the biomarker identification program 110 may have generated 1000 cumulant groups and of those 1000 cumulant groups the biomarker identification program 110 may determine 400 significant higher-order cumulant groups. As will be explained in more detail below, the features of the significant higher-order cumulant groups may also be evaluated for significance.

The biomarker identification program 110 may evaluate each pair of features for the one or more significant higher-order joint cumulant groups. The biomarker identification program 110 may evaluate the significance of each pair of features for the significant higher-order cumulant groups. The biomarker identification program 110 may determine whether each pair of features of the significant higher-order joint cumulant groups are significant based on at least, the number of significant-higher order joint cumulant groups in which both features are present, the number of significant-higher order joint cumulant groups in which each feature appears without the other feature, and the number of groups in which neither of the features appear. The biomarker identification program 110 may utilize the feature pair of feature occurrence to determine p-values for feature pairs from a statistical significance test, such as, but not limited to, a Fisher's Exact test. The statistical significance test may utilize a confusion matrix as input, wherein the confusion matrix may be based on the pairs of feature occurrences in the one or more significant higher-order joint cumulant groups. The biomarker identification program 110 may utilize a significance feature threshold in determining whether each pair of features is significant, the significance feature threshold may be a p-value which the pair of features may not exceed in order to be embedded in a lower dimensional network, as will be explained in more detail below.

For example, there may be 400 significant higher-order cumulant groups with a p-value and Z-score within the significance threshold. The significant higher-order cumulant groups within the significance threshold may have a p-value lower than the threshold p-value and a Z-score greater than the threshold Z-score. Within the 400 significant higher-order cumulant groups there may be 100 features represented in some combination. Significant Higher-Order Joint Cumulant Group 1 may include Feature 1, Feature 3, Feature 40, and Feature 99. Significant Higher-Order Joint Cumulant Group 2 may include Feature 1, Feature 3, Feature 77, and Feature 88. In this example, Feature 1 may be the SAMD1 gene and Feature 3 may be NP1URIN phenotype. The biomarker identification program 110 may determine that of the 400 significant higher-order cumulant groups Feature 1 and Feature 3 appear together in 200 significant higher-order joint cumulant groups, Feature 1 appears without Feature 3 in 20 significant higher-order joint cumulant groups, Feature 3 appears without Feature 1 in 30 significant higher-order joint cumulant groups, and there are 150 significant higher-order joint cumulant groups in which neither Feature 1 nor Feature 3 are present. The biomarker identification program 110 may utilize these determinations as the confusion matrix in which the Fisher Exact test determines the p-value for the Feature 1 and Feature 3 pair to be 1.8e-55, which is within the significance feature threshold of the biomarker identification program 110 and the interaction between Feature 1 and Feature 3 may be embedded with the significant higher-order joint cumulant group into a lower dimensional network.

At 206, the biomarker identification program 110 embeds the one or more significant higher-order joint cumulant groups into a lower dimensional network. The biomarker identification program 110 may embed the feature pairs of the significant higher-order cumulant groups within the significance feature threshold.

The biomarker identification program 110 may preserve the higher-order interaction information when embedding the one or more significant higher-order joint cumulants into the lower dimensional network. The network may be a graphical representation of the relationships between significant feature pairs of the one or more significant higher-order cumulant groups. As will be explained in more detail below with respect to step 210, the biomarker identification program 110 may display the results to the user using a Maximum Spanning Tree (MST) graphical representation of the network.

At 208, the biomarker identification program 110 identifies one or more biomarkers. The biomarker identification program 110 may identify the one or more biomarkers based on a selection and/or input of the user (e.g., genetic counselor, doctor, patient, researcher, patient, medical professional) in the complex disease dashboard 118. The selection and/or input of the user (e.g., genetic counselor, doctor, patient, researcher, patient, medical professional) may be based on patient data.

The patient data may be data such as electronic health records (EHRs), diet data, lifestyle data, demographics, medications, amongst other patient-centric health data. The biomarker identification program 110 may integrate the patient data into the network generated in steps 202 through 206. The user (e.g., genetic counselor, doctor, patient, researcher, patient, medical professional) may identify one or more biomarkers for the patient data based on symptoms for the complex disease.

At 210, the biomarker identification program 110 displays results to a user. The biomarker identification program 110 may display the results to the user in the complex disease dashboard 118 based on the one or more biomarkers identified at step 208. The results displayed by the biomarker identification program 110 may include, but are not limited to including, phenotype patterns, genotypes associated with the phenotype patterns, amongst other results associated with the one or more biomarkers.

The biomarker identification program 110 may display the results to the user in one or more formats, the one or more formats including, but not limited to, graphical formats. The biomarker identification program 110 may display the significant features of the significant higher-order joint cumulant groups as nodes within the graphical format. The edges between nodes may be utilized in displaying the significance of the feature pair between nodes. For example, the edges between more significant feature pairs may be thicker than the edges between less significant feature pairs.

The biomarker identification program 110 may also utilize additional features in displaying the results to the user, such as different colors for genes and phenotypes, as well as different colors for nodes which may indicate the number of related features for a node.

The biomarker identification program 110 may display the results to the user using a Maximum Spanning Tree (MST) of the network. The biomarker identification 110 may generate the MST of the network using one or more machine learning algorithms, such as, but not limited to, Prim's algorithm and/or Kuskal's algorithm. The biomarker identification program 110 may utilize the MST to display only a limited number of edges between features. For example, the top 20% of edges present may be displayed.

The biomarker identification program 110 may display the results to the user using at least, therapies, prognosis, genetics, and/or hypothesis. For example, for a gene of interest the user may select and/or enter the gene in the complex disease dashboard 118 and the biomarker identification program 110 may display the gene as part of the network to the user through the complex disease dashboard 118.

It may be appreciated that FIG. 2 provides only an illustration of one embodiment and do not imply any limitations with regard to how different embodiments may be implemented. Many modifications to the depicted embodiment(s) may be made based on design and implementation requirements.

Figure 3:
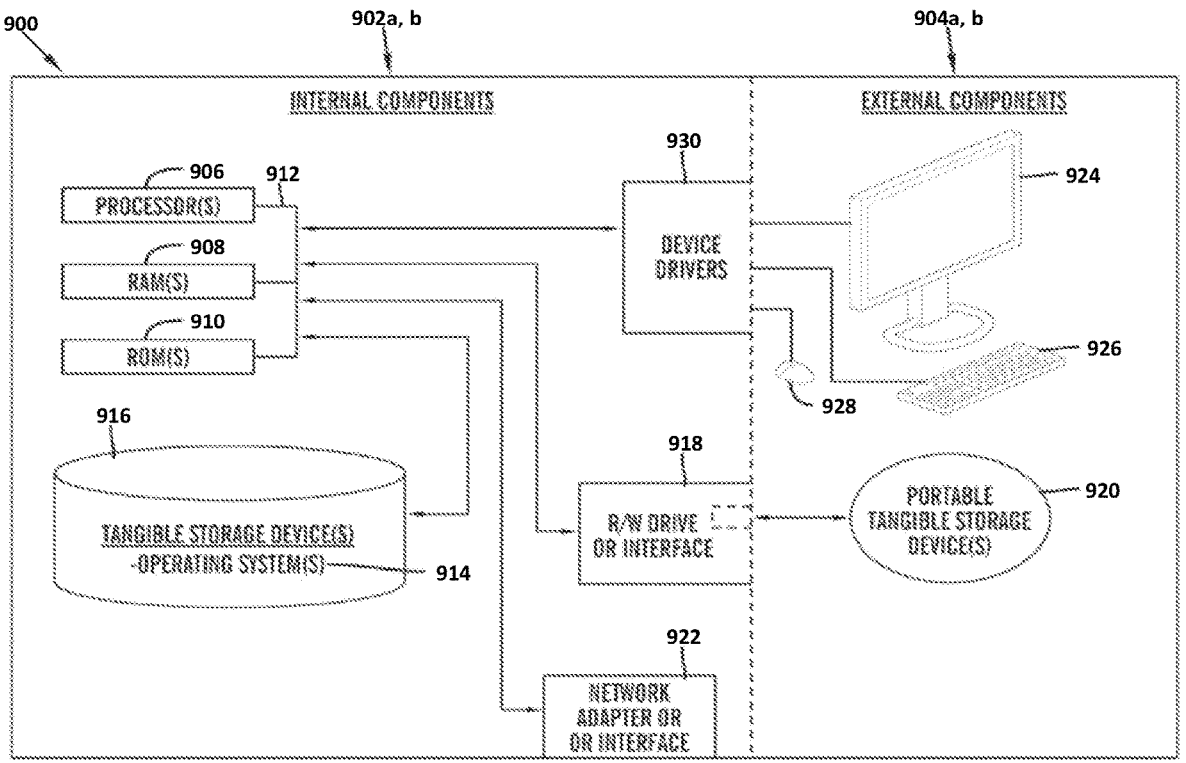
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 3. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the biomarker identification program 110a in client computer 102, and the biomarker identification program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the biomarker identification program 110a and 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The software program 108 and the biomarker identification program 110a in client computer 102 and the biomarker identification program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the biomarker identification program 110a in client computer 102 and the biomarker identification program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
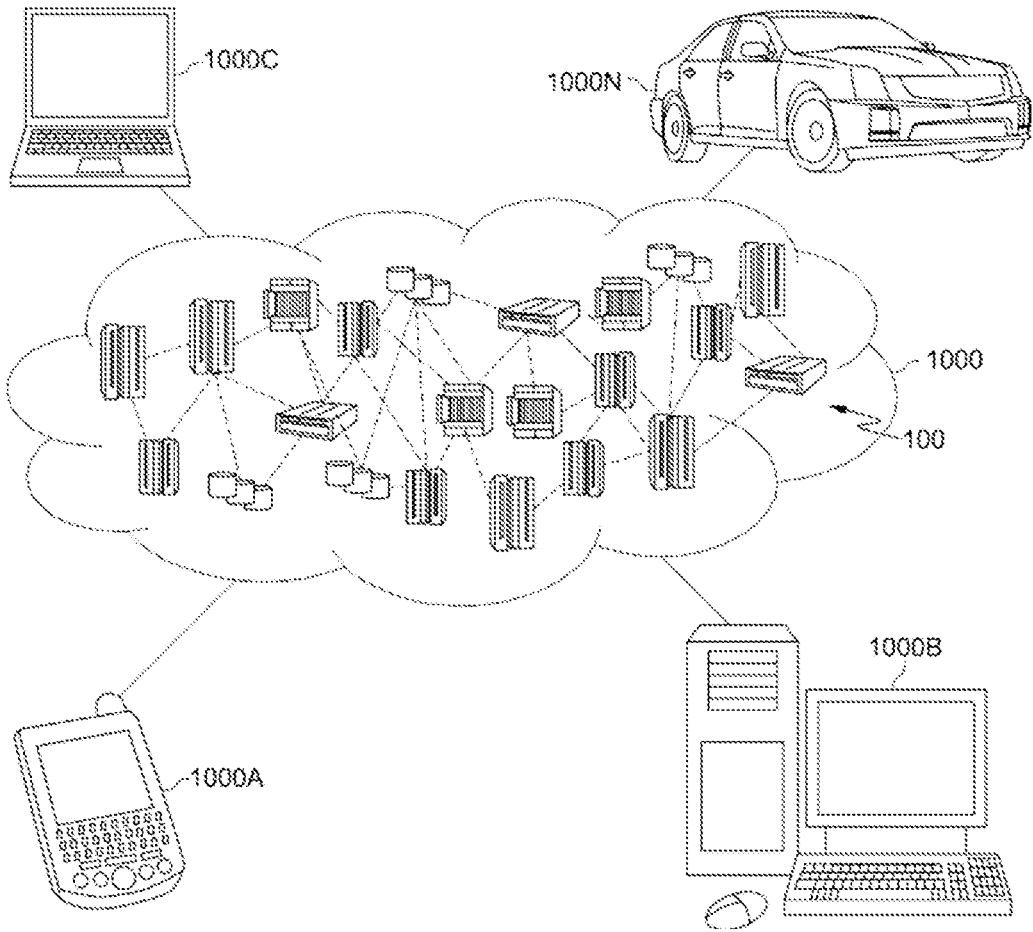
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
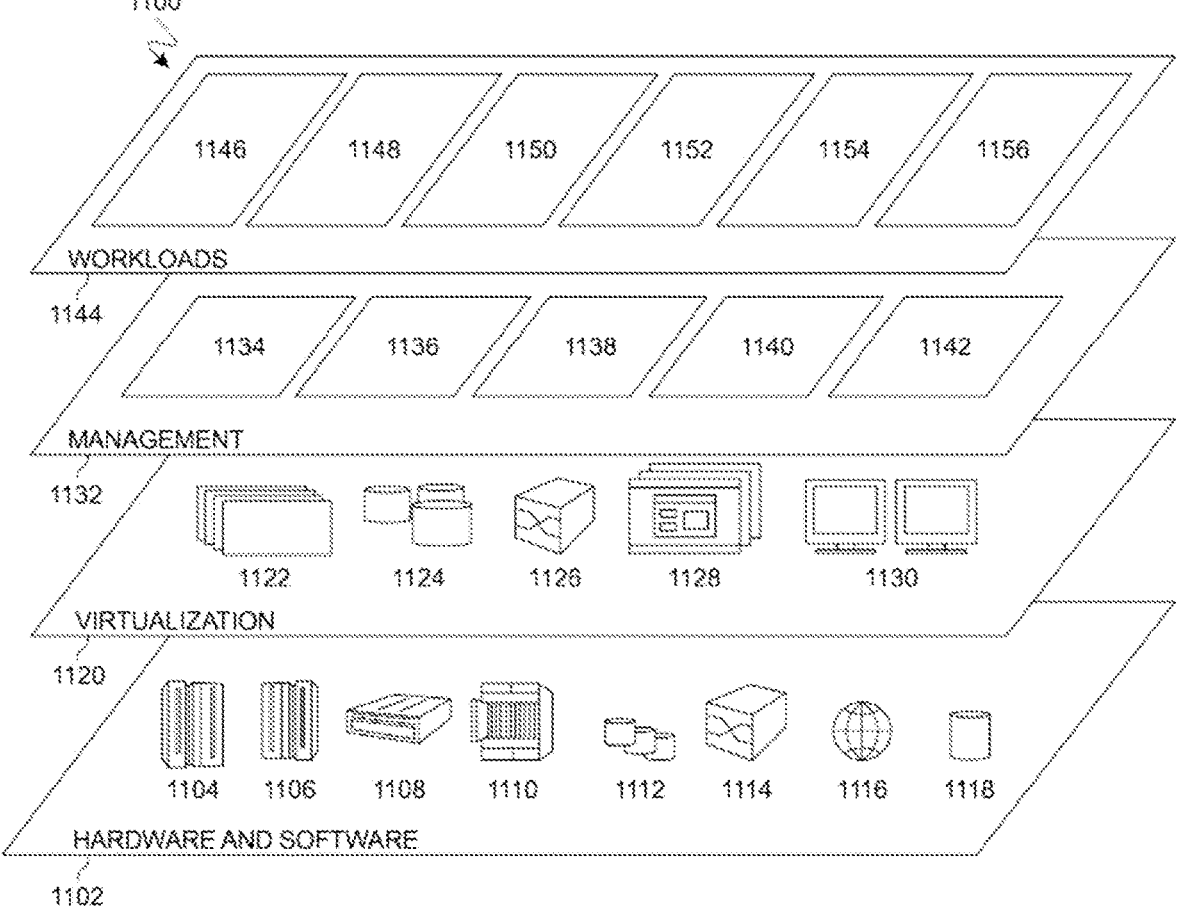
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and biomarker identification program 1156. A biomarker identification program 110*a*, 110*b* provides a way to maintain higher order interactions between features in a lower dimensional network.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

The present disclosure shall not be construed as to violate or encourage the violation of any local, state, federal, or international law with respect to privacy protection.

What is claimed is:

1. A method for biomarker identification, the method comprising:

generating a plurality of higher-order joint cumulants based on an input data matrix;

identifying one or more significant higher-order joint cumulant groups by performing one or more permutation tests using one or more significant subsets of features from the plurality of higher-order joint cumulants, wherein the one or more significant subsets of features are determined based on p- values and Z-scores, wherein the p-values are a probability of obtaining a result at least as extreme as observed results, and wherein the Z-scores denote the result in standard deviations away from an arithmetic mean under null hypotheses;

embedding the one or more significant higher-order joint cumulant groups into a lower dimensional network;

identifying one or more biomarkers based on a plurality of nodes of the one or more significant higher-order joint cumulant groups in the lower dimensional network; and displaying results to a user, wherein the results are displayed to the user in a complex disease dashboard.

2. The method of claim 1, wherein the input data matrix is generated based on biomedical data accessed from a knowledge corpus, wherein the biomedical data is selected from the group consisting of clinical data, omics data, and outcome data, and wherein generating the input data matrix further comprises:

performing an expression quantitative trait loci (eQTL) analysis and a genome wide association study analysis on the biomedical data accessed from the knowledge corpus.

3. The method of claim 1, wherein the one or more significant higher-order joint cumulant groups are a redescription cluster of features constructed from interactions between the plurality of higher-order joint cumulants between clinical features and genes selected by the user in the complex disease dashboard, and wherein identifying the one or more significant higher-order joint cumulant groups further comprises:

performing a Cumulant-based Network analysis (CuNa).

4. The method of claim 1, wherein edges between the plurality of nodes of the one or more significant higher-order joint cumulant groups are utilized in displaying a significance of a feature pair between nodes, and wherein a Maximum Spanning Tree (MST) of the lower dimensional network is utilized in the displaying of the results to the user.

5. The method of claim 4, wherein the MST includes a limited number of edges between features and is generated using Prim's algorithm or Kuskal's algorithm.

6. The method of claim 1, wherein the one or more permutation tests include at least Fisher permutation tests and utilize a Fisher-Yates shuffle for randomization.

7. The method of claim 1, wherein each of the one or more significant higher-order joint cumulant groups include a p-value and a Z-score above a significance threshold.

8. The method of claim 1, wherein the results displayed to the user include phenotype patterns and genotypes associated with the phenotype patterns for each of the one or more biomarkers identified.

9. A computer system for biomarker identification, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

generating a plurality of higher-order joint cumulants based on an input data matrix;

identifying one or more significant higher-order joint cumulant groups by performing one or more permutation tests using one or more significant subsets of features from the plurality of higher-order joint cumulants, wherein the one or more significant subsets of features are determined based on p-values and Z-scores, wherein the p-values are a probability of obtaining a result at least as extreme as observed results, and wherein the Z-scores denote the result in standard deviations away from an arithmetic mean under null hypotheses;

embedding the one or more significant higher-order joint cumulant groups into a lower dimensional network;

identifying one or more biomarkers based on a plurality of nodes of the one or more significant higher-order joint cumulant groups in the lower dimensional network; and displaying results to a user, wherein the results are displayed to the user in a complex disease dashboard.

10. The computer system of claim 9, wherein the input data matrix is generated based on biomedical data accessed from a knowledge corpus, wherein the biomedical data is selected from the group consisting of clinical data, omics data, and outcome data, and wherein generating the input data matrix further comprises:

performing an expression quantitative trait loci (eQTL) analysis and a genome wide association study analysis on the biomedical data accessed from the knowledge corpus.

11. The computer system of claim 9, wherein the one or more significant higher-order joint cumulant groups are a redescription cluster of features constructed from interactions between the plurality of higher-order joint cumulants between clinical features and genes selected by the user in the complex disease dashboard, and wherein identifying the one or more significant higher-order joint cumulant groups further comprises:

performing a Cumulant-based Network analysis (CuNa).

12. The computer system of claim 9, wherein edges between the plurality of nodes of the one or more significant higher-order joint cumulant groups are utilized in displaying a significance of a feature pair between nodes, and wherein a Maximum Spanning Tree (MST) of the lower dimensional network is utilized in the displaying of the results to the user.

13. The computer system of claim 12, wherein the MST includes a limited number of edges between features and is generated using Prim's algorithm or Kuskal's algorithm.

14. The computer system of claim 9, wherein the one or more permutation tests include at least Fisher permutation tests and utilize a Fisher-Yates shuffle for randomization, wherein each of the one or more significant higher-order joint cumulant groups include a p-value and a Z-score above a significance threshold, and wherein the results displayed to the user include phenotype patterns and genotypes associated with the phenotype patterns for each of the one or more biomarkers identified.

15. A computer program product for biomarker identification, comprising:

one or more non-transitory computer-readable storage media and program instructions stored on at least one of the one or more tangible storage media, the program instructions executable by a processor to cause the processor to perform a method comprising:

generating a plurality of higher-order joint cumulants based on an input data matrix;

identifying one or more significant higher-order joint cumulant groups by performing one or more permutation tests using one or more significant subsets of features from the plurality of higher-order joint cumulants, wherein the one or more significant subsets of features are determined based on p- values and Z-scores, wherein the p-values are a probability of obtaining a result at least as extreme as observed results, and wherein the Z-scores denote the result in standard deviations away from an arithmetic mean under null hypotheses;

embedding the one or more significant higher-order joint cumulant groups into a lower dimensional network;

identifying one or more biomarkers based on a plurality of nodes of the one or more significant higher-order joint cumulant groups in the lower dimensional network; and displaying results to a user, wherein the results are displayed to the user in a complex disease dashboard.

16. The computer program product of claim 15, wherein the input data matrix is generated based on biomedical data accessed from a knowledge corpus, wherein the biomedical data is selected from the group consisting of clinical data, omics data, and outcome data, and wherein generating the input data matrix further comprises:

performing an expression quantitative trait loci (eQTL) analysis and a genome wide association study analysis on the biomedical data accessed from the knowledge corpus.

17. The computer program product of claim 15, wherein the one or more significant higher-order joint cumulant groups are a redescription cluster of features constructed from interactions between the plurality of higher-order joint cumulants between clinical features and genes selected by the user in the complex disease dashboard, and wherein identifying the one or more significant higher-order joint cumulant groups further comprises:

performing a Cumulant-based Network analysis (CuNa).

18. The computer program product of claim 15, wherein edges between the plurality of nodes are utilized in displaying a significance of a feature pair between nodes, and wherein a Maximum Spanning Tree (MST) of the lower dimensional network is utilized in the displaying of the results to the user.

19. The computer program product of claim 18, wherein the MST includes a limited number of edges between features and is generated using Prim's algorithm or Kuskal's algorithm.

20. The computer program product of claim 15, wherein the one or more permutation tests include at least Fisher permutation tests and utilize a Fisher-Yates shuffle for randomization, wherein each of the one or more significant higher-order joint cumulant groups include a p-value and a Z-score above a significance threshold, and wherein the results displayed to the user include phenotype patterns and genotypes associated with the phenotype patterns for each of the one or more biomarkers identified.

*   *   *   *   *